US007743660B2

(12) United States Patent
Marsh et al.

(10) Patent No.: US 7,743,660 B2
(45) Date of Patent: Jun. 29, 2010

(54) SYSTEM AND METHOD FOR AUTOMATED INSPECTION OF LARGE-SCALE PART

(75) Inventors: Bobby J. Marsh, Lake Stevens, WA (US); Kinson D. Vanscotter, Stanwood, WA (US); Leonard S. Bodziony, Seattle, WA (US); Gary E. Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 398 days.

(21) Appl. No.: 11/818,807

(22) Filed: Jun. 15, 2007

(65) Prior Publication Data

US 2008/0307886 A1    Dec. 18, 2008

(51) Int. Cl.
    *G01N 29/265*    (2006.01)
(52) U.S. Cl. .................. 73/633; 73/634; 73/865.5; 73/865.8
(58) Field of Classification Search ................ 73/865.5, 73/865.8, 633, 634
    See application file for complete search history.

(56) References Cited

U.S. PATENT DOCUMENTS

| | | | | |
|---|---|---|---|---|
| 4,793,185 | A | * | 12/1988 | Boettger et al. ............... 73/643 |
| 5,970,438 | A | * | 10/1999 | Clark et al. .................. 702/184 |
| 6,166,811 | A | | 12/2000 | Long et al. |
| 6,220,099 | B1 | * | 4/2001 | Marti et al. .................... 73/633 |
| 6,378,387 | B1 | * | 4/2002 | Froom ........................ 73/865.8 |
| 6,643,002 | B2 | * | 11/2003 | Drake, Jr. ..................... 356/72 |
| 6,681,145 | B1 | | 1/2004 | Greenwood et al. |
| 6,907,799 | B2 | * | 6/2005 | Jacobsen et al. ............ 73/865.8 |
| 7,277,811 | B1 | | 10/2007 | Marsh |
| 7,454,265 | B2 | | 11/2008 | Marsh |
| 7,587,258 | B2 | | 9/2009 | Marsh |
| 2001/0045125 | A1 | * | 11/2001 | Alexander .................... 73/146 |
| 2003/0192382 | A1 | * | 10/2003 | Mueller ........................ 73/620 |
| 2007/0006658 | A1 | * | 1/2007 | Kennedy et al. .............. 73/622 |
| 2008/0310754 | A1 | | 12/2008 | Safai et al. |

OTHER PUBLICATIONS

International Search Report and Written Opinion of the International Searching Authority, European Patent Office, Oct. 21, 2008, Int. Application No. PCT/US2008/067019, (15 pgs).
Reich et al., 3-D Shape Measurement of Complex Objects by Combining Photogrammetry and Fringe Projection, Optical Engineering, Jan. 2000, vol. 39—No. 1, Society of Photo-Optical Instrumentation Engineers (8 pgs).

* cited by examiner

*Primary Examiner*—Hezron Williams
*Assistant Examiner*—Rose M Miller
(74) *Attorney, Agent, or Firm*—Toler Law Group

(57) ABSTRACT

Systems and methods can automatically inspect a workpiece. Non-destructive inspection sensors are mounted on a frame mounted on a transport device. Position of a first predetermined location of a workpiece is measured with a tracking system. The transport device is moved to position the non-destructive inspection sensors proximate the first predetermined location of a workpiece. A first portion of a workpiece proximate the first predetermined location is non-destructively inspected with the non-destructive inspection sensors. Position of a second predetermined location of a workpiece can be measured with the tracking system. The transport device can be moved to position the non-destructive inspection sensors proximate the second predetermined location of a workpiece, and a second portion of a workpiece proximate the second predetermined location can be non-destructively inspected with the non-destructive inspection sensors. Data can be provided from the sensors to a computing system and analyzed by the computing system.

45 Claims, 9 Drawing Sheets

SYSTEM AND METHOD FOR AUTOMATED INSPECTION OF LARGE-SCALE PART

BACKGROUND

Several methods of performing non destructive inspection (NDI) have been developed and currently are in use in a variety of manufacturing settings. Some of these NDI methods include, without limitation, ultrasound inspection, mechanical tap testing, acoustic impact Doppler, eddy current testing optical sensing, x-ray backscatter, photon induced positron annihilation, laser shearography, infrared thermography, neutron radiography, through-transmission infrared thermography, and the like. Many individual NDI methods may be better-suited to inspection of a particular material than other materials.

The above and other NDI methods make use of sensor positional information to produce two-dimensional and three-dimensional image data regarding possible internal damage or possible defects in various structural materials. Position of the sensors typically is tracked by positional encoders mounted on robotic arms or X-Y-Z bridges, thereby resulting in substantially manual NDI processes. As sizes of parts to be inspected increase, improvements may be made in terms of cost, speed of inspection, versatility, and interchangeability.

The foregoing examples of related art and limitations associated therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems and methods which are meant to be exemplary and illustrative, not limiting in scope. In various embodiments, one or more of the problems described above in the Background have been reduced or eliminated, while other embodiments are directed to other improvements.

According to exemplary embodiments, systems and methods can automatically inspect a workpiece. Non-destructive inspection sensors are mounted on a frame that is mounted on a transport device. Position of a first predetermined location of a workpiece is measured with a tracking system. The transport device is moved to position the non-destructive inspection sensors proximate the first predetermined location of a workpiece, and a first portion of a workpiece proximate the first predetermined location is non-destructively inspected with the non-destructive inspection sensors.

According to an aspect, the sensors can be automatically moved and tracked. Position of a second predetermined location of a workpiece can be measured with the tracking system. The transport device can be moved to position the non-destructive inspection sensors proximate the second predetermined location of a workpiece, and a second portion of a workpiece proximate the second predetermined location can be non-destructively inspected with the non-destructive inspection sensors.

According to another aspect, data from the sensors can be analyzed. Data can be provided from the non-destructive inspection sensors to a computing system and the data can be analyzed with the computing system. The data can be compared with predetermined threshold criteria for a workpiece. Further, a workpiece can be marked in an associated location when analyzed data for the associated location is outside the predetermined threshold criteria.

In another exemplary embodiment, a system is provided for automatically inspecting a workpiece. The system includes a tracking system, a transport device, and a frame that is mounted on the transport device. The frame has a shape that accommodates a shape of an exterior of a workpiece to be inspected. The system also includes non-destructive inspection sensors mounted on the frame and a computing system that is operatively coupled to the tracking system and to the non-destructive inspection sensors.

According to an aspect, sensors for several types of non-destructive inspection methods can be used. Further, the non-destructive inspection sensors can include at least one sensor for a first type of non-destructive inspection and at least one sensor for a second type of non-destructive inspection that is different from the first type of non-destructive inspection.

In addition to the exemplary embodiments and aspects described above, further embodiments and aspects will become apparent by reference to the drawings and by study of the following detailed description.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DETAILED DESCRIPTION

By way of overview, systems and methods can automatically inspect a workpiece. Non-destructive inspection sensors are mounted on a frame that is mounted on a transport device. Position of a first predetermined location of a workpiece is measured with a tracking system. The transport device is moved to position the non-destructive inspection sensors proximate the first predetermined location of a workpiece, and a first portion of a workpiece proximate the first predetermined location is non-destructively inspected with the nondestructive inspection sensors. The sensors can be automatically moved and tracked. Position of a second predetermined location of a workpiece can be measured with the tracking system. The transport device can be moved to position the non-destructive inspection sensors proximate the second predetermined location of a workpiece, and a second portion of a workpiece proximate the second predetermined location can be non-destructively inspected with the non-destructive inspection sensors. Details will be set forth below.

Figure 1:
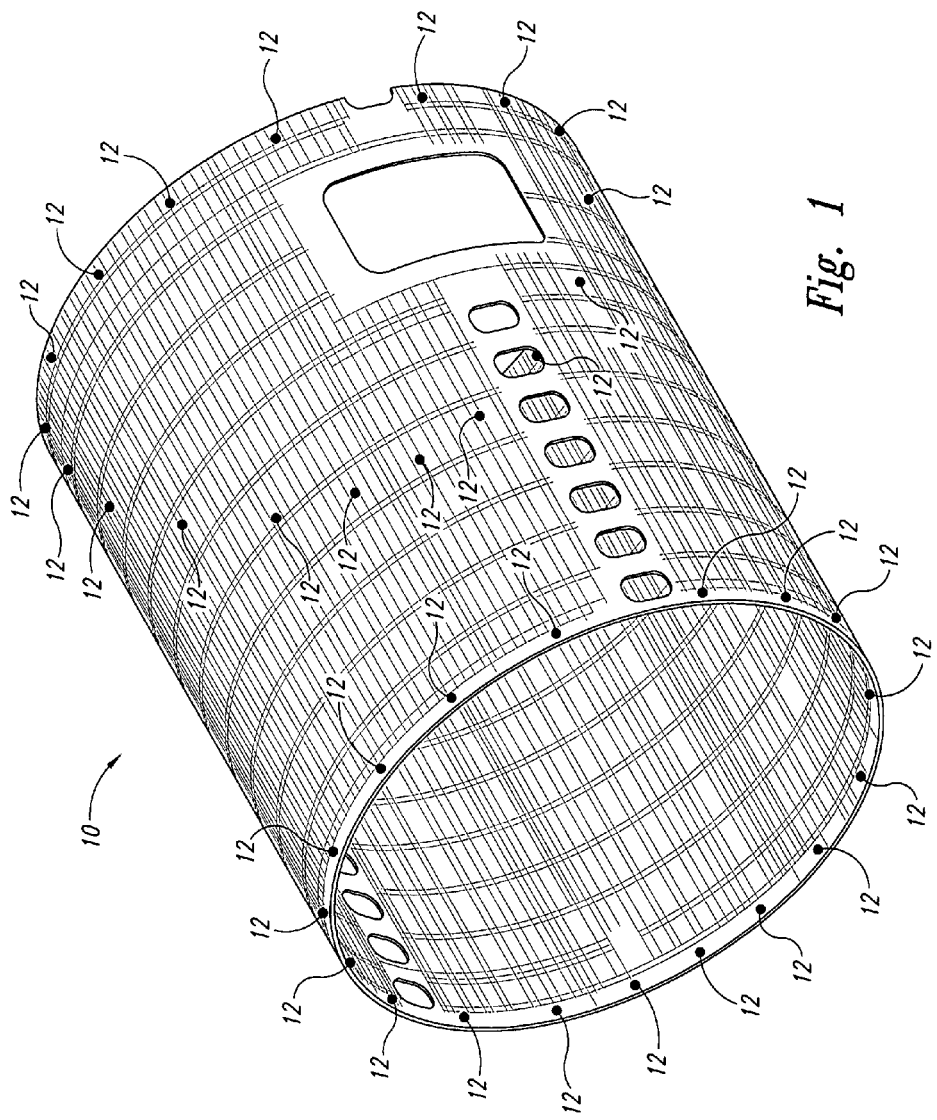
FIG. 1 is a perspective view of an exemplary part to be inspected.

Referring to FIG. 1, an exemplary workpiece 10 can be automatically inspected. The workpiece 10 may be a large-scale part, thereby taking advantage of automation provided by embodiments disclosed herein. Given by way of non-limiting example for illustration purposes only and not by way of limitation, the workpiece 10 may be an aircraft part, such as without limitation a section of an aircraft fuselage. The workpiece 10 is illustrated herein in the form of an aircraft fuselage for illustrative purposes only. It will be understood that the workpiece 10 can be any type of workpiece as desired. For example, the workpiece 10 can be a wing of an aircraft or other part of an aircraft. Further, the workpiece 10 need not be related to an aircraft, and can be a part of any vehicle or structure. Moreover, the workpiece 10 can be an entire vehicle or structure itself. Thus, it is not intended to limit the workpiece 10 in any manner whatsoever.

Moreover, the workpiece 10 may be made of any material as desired for a particular application. It will be appreciated that the type of material used for the workpiece may, in part, determine which type of non-destructive inspection technique may be used to inspect the workpiece 10. Given by way of non-limiting examples, the workpiece 10 may be made of composite material, such as a composite laminate, or a metal, such as aluminum or titanium or the like. It will be understood that it is not intended to limit in any manner whatsoever the materials from which the workpiece 10 may be made.

In an exemplary embodiment, the workpiece 10 includes features to help confirm accuracy of measurements made thereon. For example, holes 12 are defined in predetermined locations about an exterior surface of the workpiece 10. Positioning aids, such as fiducials (not shown in FIG. 1) may be placed in the holes to help determine position of measurements, as will be discussed further below. The holes 10 suitably are components of a part reference system, such as a determinant assembly coordinate system, in which parts are referenced to each other (as opposed to the parts being referenced to assembly tooling). The part reference system suitably indexes location of each of the holes 10 in three dimensions—an A dimension, a B dimension, and a C dimension. However, any indexing technique may be used as desired for a particular application.

Figure 2:
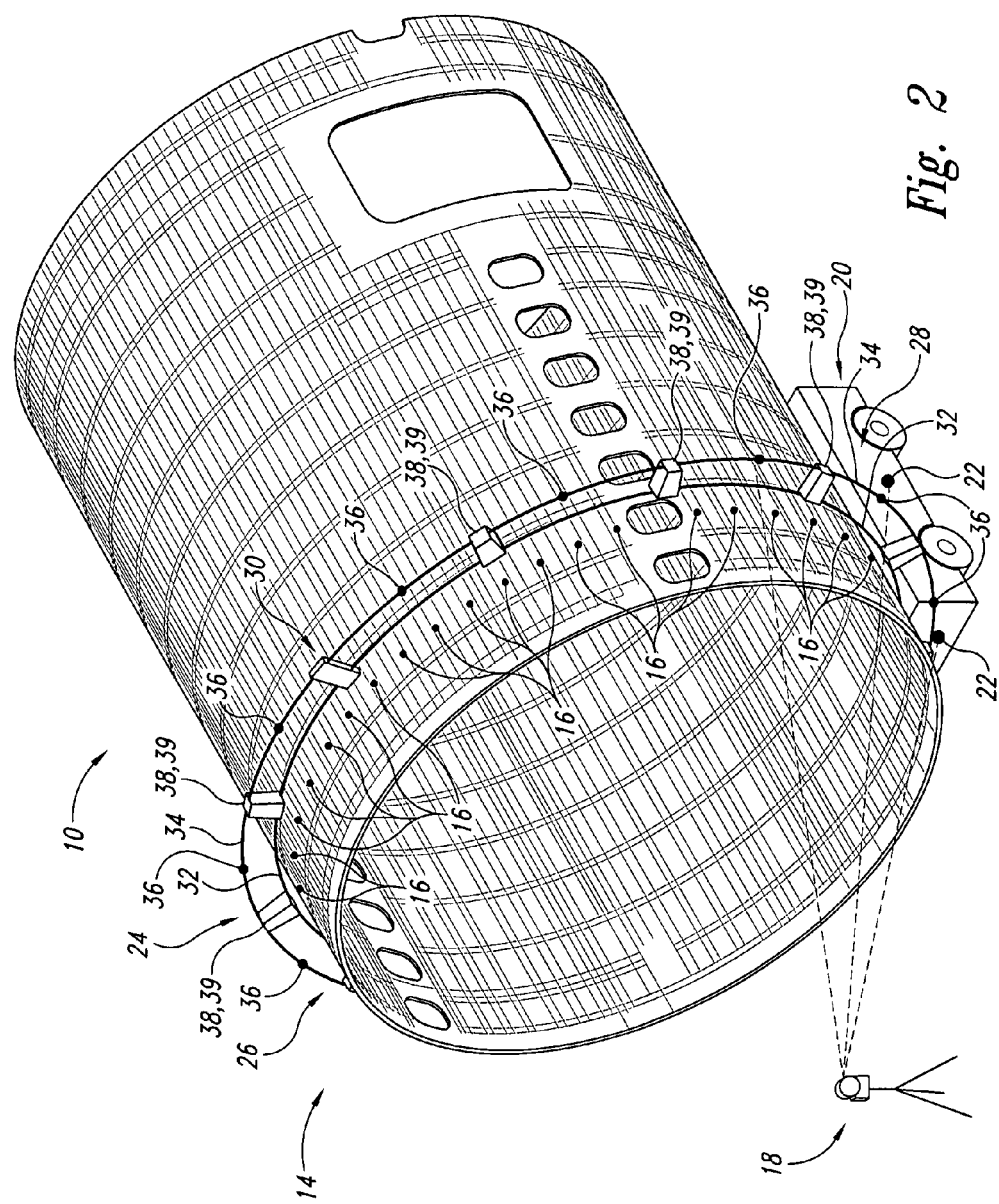
FIG. 2 is a perspective view of an exemplary part being inspected by an exemplary system.
Figure 3:
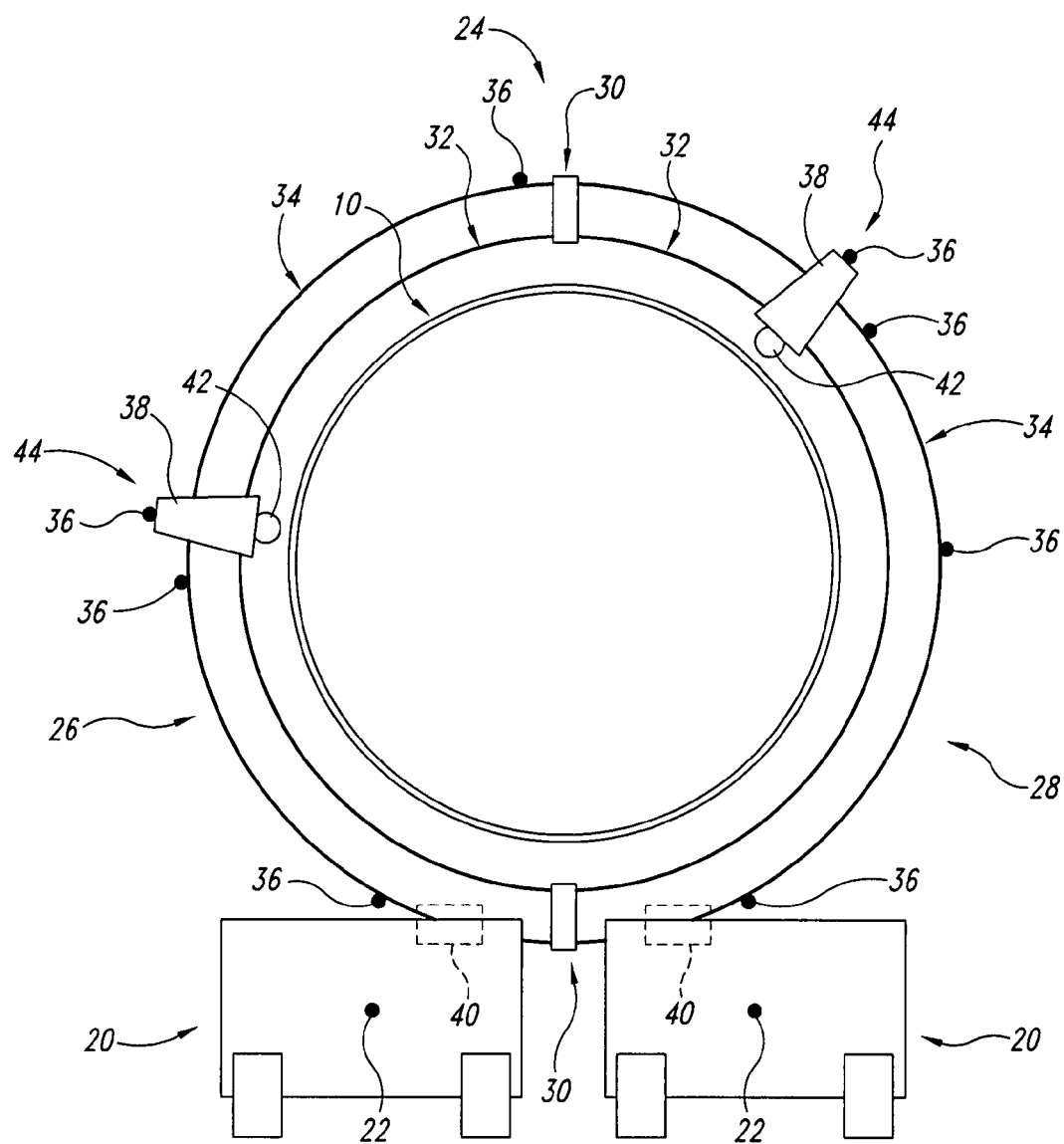
FIG. 3 illustrates an end view of the exemplary part being inspected by the exemplary system of FIG. 2.

Referring now to FIGS. 2 and 3, a system 14 can automatically inspect the workpiece 10. As discussed above, the workpiece 10 is shown as an aircraft fuselage for purposes of illustration only and not by way of limitation.

Fiducials, or targets, 116 are installed in the holes 112 (not shown in FIG. 2). The fiducials 116 may be installed in the holes using a snap-fit or other installation mechanism known in the art. The fiducials 116 may be passive reflectors that may have reflectors (not shown) that are adapted to reflect photogrammetry light beams and/or separate reflectors (not shown) which are adapted to reflect laser beams emitted from laser tracking devices. The fiducials 116 may include any of the embodiments disclosed in US Patent Application Serial fiducials 116 may include any of the embodiments disclosed in U.S. patent application Ser. No. 11/437,201 filed May 19, 2006, and entitled "Combination Laser and Photogrammetry Target," the detailed description of which is included below.

Figure 7:
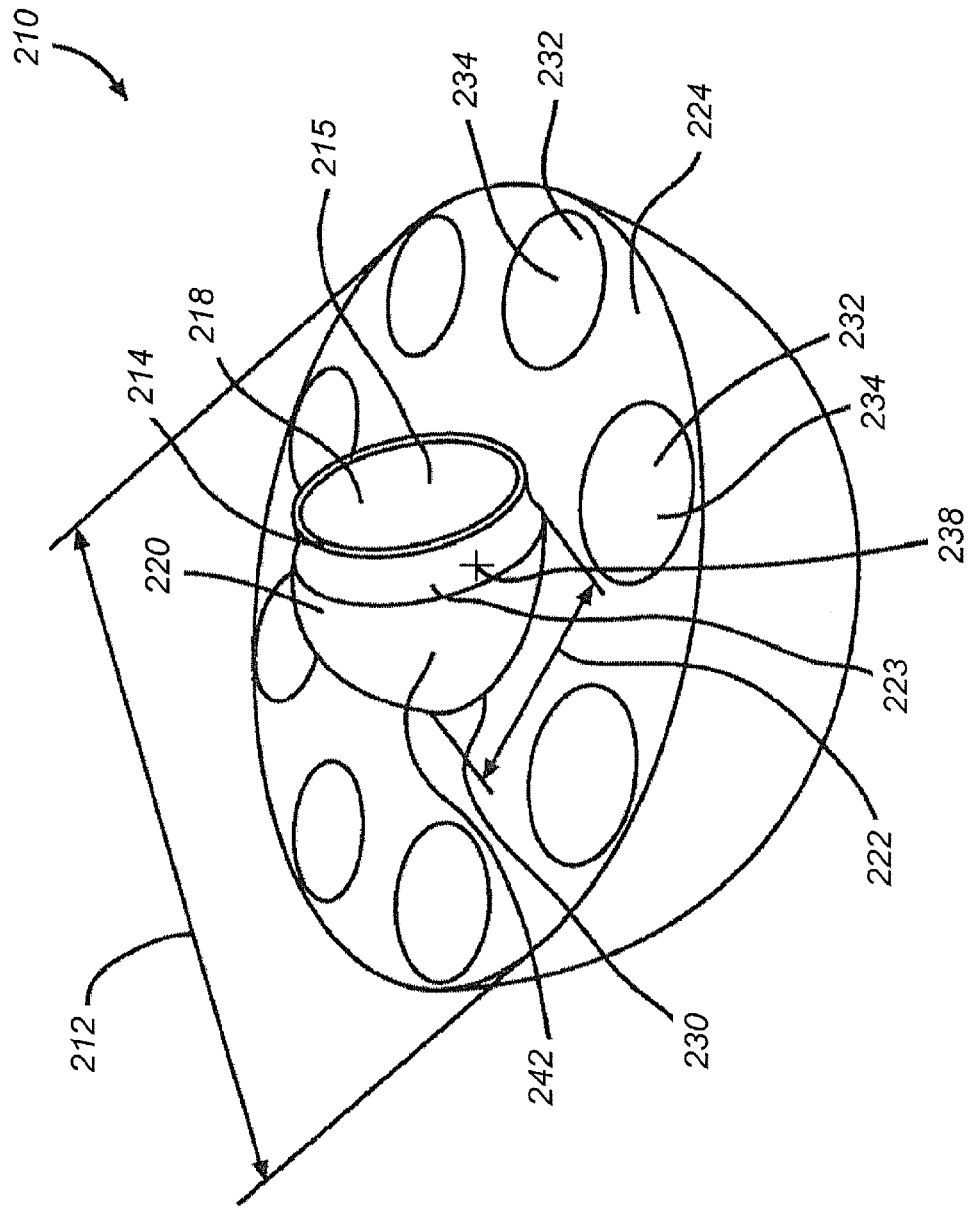
FIG. 7 is a perspective view of one embodiment of a target.
Figure 8:
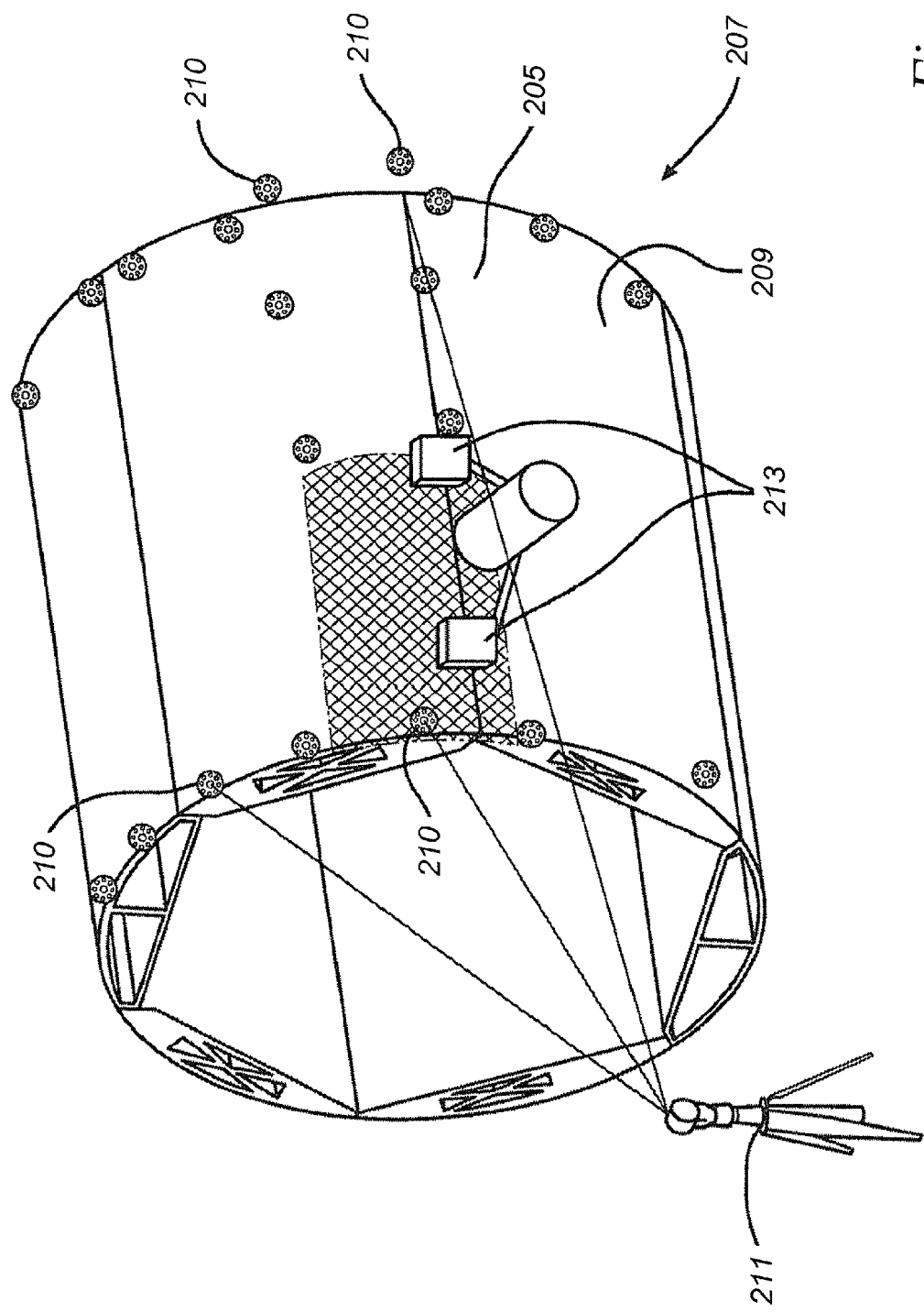
FIG. 8 is a perspective view showing a plurality of the target of FIG. 7 being distributed around a barrel of an airplane to measure a surface of the barrel.

In one embodiment of the invention, as shown in FIG. 7, a target 210 for use in measuring surfaces may have a generally hemispherical shape. As shown in FIG. 8, a plurality of the target 210 of FIG. 7 may be distributed over a surface 205 of an airplane 207, which may comprise an airplane's barrel 219, to measure the surface 215. In other embodiments, one or more targets 210 may be used to measure one or more surfaces in non-airplane applications. One or more locations of the targets 210, distributed over surface 215, may be measured utilizing a combination of a laser tracking device 211 and a photogrammetry device 213. The measured locations of the targets 210 may be utilized to determine the measurements of the surface 215.

In one embodiment, the photogrammetry device 213 may comprise one or more V-Star cameras. In other embodiments, the photogrammetry device 213 may comprise any photogrammetry device known in the art. The target 210 may be made of steel, and may have a diameter 212 substantially in the range of one-half of an inch to two inches. In other embodiments, the target 210 may be made of any material known in the art, and may be in differing shapes, sizes, orientations, and configurations.

The target 210 may comprise a first portion 214 and a second portion 232. The first portion 214 may comprise one or more surfaces 215 which are adapted to reflect a laser beam towards laser tracking device 211. In one embodiment, the first portion 214 may comprise three reflective mirrors 218 attached to a generally spherical surface 220. The first portion 214 may comprise a spherical magnetic reflector (SMR). In other embodiments, any number of mirrors 218 may be utilized, and the mirrors 218 may be attached to differing sized and shaped surfaces of the target 210. In still other embodiments, the first portion 214 may comprise one or more non-mirror reflective surfaces.

The generally spherical surface 220 may have a diameter 222 in the range of one-eighth of an inch to one-inch. In other embodiments, the diameter 222 of the spherical surface 220 may be in varying sizes. The first portion 214 may be located in a center 223 of a surface 224 of the target 210. In other embodiments, first portion 214 may be located in varying portions of the target 210.

The first portion 214 may be attached to the target 210 utilizing one or more magnets (not shown). The one or more magnets may be attached to a surface of an aperture 230 in the target 210 utilizing adhesive, a snap-fit, or other devices known in the art. Aperture 230 may be centrally located with respect to target 210. In other embodiments, first portion 214 may be attached to the target 210 utilizing other devices known in the art. First portion 214 may be adapted to move, relative to both target 210 and second portion 232, into varying planes. The first portion 214 may be adapted to rotate in a variety of directions in order to be located in the same or different planes as second portion 232. In one embodiment, a user of target 210 may rotate first portion 214 utilizing the user's hand.

The second portion 232 may comprise one or more discrete surfaces 234 which are adapted to reflect a light beam towards a photogrammetry device 213, such as one or more V-Star cameras. In one embodiment, the second portion 232 may comprise one or more reflective surfaces 234, adhered to one or more surfaces 224 of the target 210. In other embodiments, reflective surfaces 234 may be attached to target 210 utilizing any manner known in the art. Reflective surfaces 234 may be made of retro-reflective material. In other embodiments, reflective surfaces 234 may be made of any reflective material known in the art.

The reflective surfaces 234 may comprise a plurality of discrete, generally circular, reflective surfaces (dots). In other embodiments, the reflective surfaces 234 may comprise three to seven generally circular, reflective surfaces (dots). In still other embodiments, the reflective surfaces 234 may comprise three to ten generally circular, reflective surfaces (dots). The generally circular, reflective surfaces (dots) may have diameters in the range of one-tenth of an inch to one-half of an inch. In still other embodiments, any number of reflective surfaces 234 may be utilized in any shape, location, orientation, size, or configuration. The second portion 232 may be evenly distributed around first portion 214. First and second portions 214 and 232 may share a common central point 238 which may be located in a center of target 210. In one embodiment, first portion 214 may be located in a central area 242 with respect to a plurality of reflective surfaces 234, and target 210. In other embodiments, first and second portions 214 and 232 may be located in a variety of locations, configurations, and orientations with respect to target 210 and with respect to one another.

Figure 9:
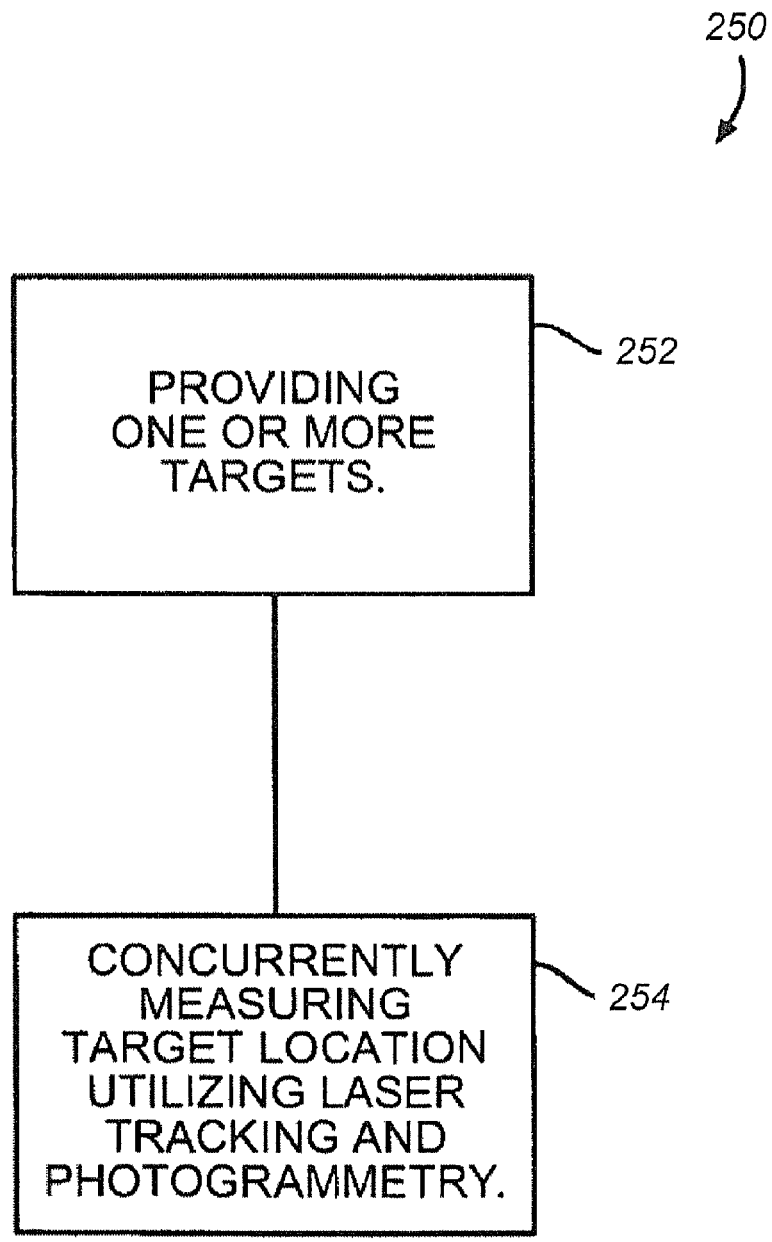
FIG. 9 depicts one embodiment of a method for measuring a surface.

In another embodiment of the invention, as depicted in FIG. 9, a method 250 for measuring a surface may be provided. The surface to be measured may comprise one or more parts of an airplane. In other embodiments, the surface to be measured may comprise a non-airplane application. One step 252 of the method may comprise providing one or more targets. The provided targets may comprise any of the embodiments of the target 210 disclosed within this specification. In one embodiment, each of the one or more targets 210 may comprise a first reflective portion 214 and a second reflective portion 232.

The provided targets may be distributed over various portions of the surface to be measured. In one embodiment, eighteen targets may be distributed around the circumference of an aft end of a barrel of an airplane, and another eighteen targets may be distributed around the circumference of the forward end of the barrel. In yet another embodiment, substantially in the range of twenty-five to forty-five targets may be distributed around the surface to be measured. In still other embodiments, any number of targets may be located on or in any portion of the surface to be measured.

Another step 254 of the method may comprise concurrently measuring one or more locations of one or more targets utilizing both laser tracking and photogrammetry. In one embodiment, the step 254 may comprise measuring X plane, Y plane, and/or Z plane locations of one or more targets. In other embodiments, step 254 may comprise taking varying measurements of one or more target locations. During step 254, a light emitting device, such as a Prospot, may emit one or more light beams onto the surface to be measured. The one or more light beams emitted by the Prospot may take the shape of a multitude of dots, in any size or shape, distributed over the surface to be measured. In one embodiment, hundreds of light-beam dots may be directed onto the surface to be measured. The emitted light-beam dots may act as a grid system to locate one or more targets with respect to various portions of the measured surface.

During step 254, the first reflective portion of the one or more targets may reflect one or more laser beams emitted from one or more laser tracking devices back towards the one or more laser tracking devices. Simultaneously, the second reflective portion of the one or more targets may reflect one or more light beams emitted from one or more photogrammetry devices back towards the one or more photogrammetry devices. The photogrammetry devices may comprise one or more V-Star cameras. By simultaneously utilizing both photogrammetry and laser tracking, one or more location measurements of one or more targets may be arrived at using combined photogrammetry and laser tracking measurements.

The photogrammetry and laser tracking measurements may be combined into one or more measurements of the targets utilizing one or more computers to interactively communicate and determine the one or more combined target measurements. The one or more combined target measurements may be utilized to determine one or more measurements of the surface. In one embodiment, measurements of the surface may be determined in the X plane, the Y plane, and/or the Z plane. In other embodiments, varying measurements of the surface may be determined.

Combining two inspection technologies, laser tracking and photogrammetry, to determine a surface's measurements may provide more accurate measurements, more efficient measurements, more timely measurements, and/or less costly measurements.

The locations of each of the fiducials 16 are measured using a tracking system 18. Given by way of non-limiting example, the locations of one or more of the fiducials 16 may be measured utilizing laser tracking, optical triangulation, digital photogrammetry, light detection and ranging (LIDAR), radio detection and ranging (RADAR), sound navigation and ranging (SONAR), ultrasound, Indoor Global Positioning System, or other suitable techniques. In one embodiment, the tracking system 18 may be embodied as a laser tracking system. Laser tracking measurements may be taken by emitting one or more laser beams from one or more laser trackers towards the outer surface of the workpiece 10. The laser beams may be reflected off the laser reflectors of one or more of the fiducials 16 back towards the laser tracker(s), which measure one or more target locations in X, Y, and/or Z planes (or the A, B, C part reference system) based on the properties of the returned laser beam. The laser tracker may include one or more commercially available laser trackers such as the Boeing Laser Tracker (BLT), Leica laser trackers, Faro laser trackers, or the like.

In another embodiment, the tracking system 18 may be embodied as a photogrammetry tracking system. Photogrammetry measurements may be taken by emitting one or more light beams from one or more photogrammetry devices towards the outer surface of the workpiece 10. The light beams are reflected off the photogrammetry reflectors of one or more of the fiducials 16 back towards the photogrammetry devices, which measures one or more of the target locations in X, Y, and/or Z planes (or the A, B, C part reference system) based on the properties of, the returned light beams. The photogrammetry devices may include one or more commercially available cameras such as V-Star cameras or the like.

At least one transport device 20 can automatically position the non-destructive inspection sensors (discussed further below). Position of the transport device 20 is tracked by the tracking system 18 and movement of the transport device 20 is controlled (as discussed further below) as the transport device 20 is moved. To that end, at least one fiducial 22 is installed on the transport device 20. The fiducial 22 is similar to the fiducial 16, described above. The transport device 20 can be any type of transporter, track system, conveyer system, vehicle, or the like, as desired for a particular application. In one embodiment, the transport device 20 includes an automated guided vehicle (AGV), such as an OmniMove AGV available from KUKA.

A frame 24 is mounted on the transport device 20. The non-destructive inspection sensors (discussed further below) are, in turn, mounted on the frame 24. The frame 24 has a shape that accommodates the shape of the workpiece 10 such that the non-destructive inspection sensors can be placed in position to sense the exterior surface of the workpiece 10.

The shape of the frame 24 and mounting of the frame 24 onto the transport device 20 depends on the shape (and size) of the workpiece 10. Given by way of non-limiting example and not by way of limitation, the frame 24 is shown for illustration purposes only as having a ring shape. The frame 24 is shaped into a ring shape that is sized to receive therein the workpiece 10 that, in this non-limiting example, is shown for illustration purposes only as an aircraft fuselage. In this example, the frame 24 is mounted on two transport devices 20 which are shown as automated guided vehicles (only one of which is visible in FIG. 2).

In an exemplary embodiment, the frame 24 suitably may be provided as a "split ring" that includes two semi-circular frame members 26 and 28. The frame member 26 is mounted to one of the transport devices 20 (not shown in FIG. 2) and the frame member 28 is mounted to the other transport device 20. The frame members 26 and 28 are joined to each other at joints 30. In this exemplary embodiment, each of the frame members 26 and 28 suitably is made up of an inner semi-circular mounting rail 32 and an outer semi-circular mounting rail 34. However, in other embodiments the frame 24 may be provided as one frame member or as more than two frame members. Moreover, in other embodiments the frame 24 may include only one mounting rail or more than two mounting rails.

Position of the frame 24 is tracked by the tracking system 18 as the transport device 20 is moved, thereby allowing position of the non-destructive sensors mounted on the frame 24 to be tracked. Such tracking permits positioning of the non-destructive inspection sensors at predetermined locations of the exterior surface of the workpiece 10 as desired. To that end, at least one fiducial 36 is installed on the frame 24. The fiducials 36 are similar to the fiducials 16 and 22, discussed above. The fiducials 36 are installed on the frame 24 as desired. For example, in one embodiment the fiducials 36 may be mounted on the outer mounting rail 32 as shown. In other embodiments, the fiducials 36 may be mounted on the inner mounting rail 32 or any mounting rail provided, as desired for a particular application. Given by way of non-limiting example, a group of three laser tracker targets may be randomly mounted, with good separation, on each of the two semi-circular frame members 26 and 28, thereby giving the transport device 20 around a +/−0.250 inch placement tolerance.

Non-destructive inspection sensors 38 are mounted on the frame 24. Sources 39 for the non-destructive inspection modality with which the sensors 38 are associated may be co-located with the sensors 38 on the frame or may be located elsewhere in the facility, as desired for a particular application and non-destruction inspection modality. It will be appreciated that any type of non-destructive inspection sensor whatsoever can be used as desired for a particular application. That is, the type of non-destructive inspection modality to be performed and, therefore, the type of non-destructive inspection sensor 38 used may depend in part on the material used for the workpiece 10 and may further depend in part on the type of characteristic to be inspected. It will further be appreciated that more than one characteristic can be inspected. Therefore, more than one type of non-destructive inspection sensor can be mounted on the frame 24. As a result, more than one characteristic of the workpiece 10 can be inspected at the same time. Also, if desired, any number of fiducials 36 may be mounted on one or more of the non-destructive sensors 38 (in addition to or in lieu of being mounted on the frame 24) for precisely tracking position of the non-destructive sensors 38. Given by way of non-limiting example, two laser tracker targets may be mounted on a bar mounted aft of all the data gathering tools on one (or more) of the sensors 38, thereby enabling tracking of position of the sensors 38 and precise placement of the sensors 38.

Any number of the non-destructive inspection sensors 38 can be mounted on the frame as desired for a particular application. In some embodiments, a sufficient number of non-destructive inspection sensors 38 may be mounted on the frame 24 to inspect substantially all of the workpiece 10 in the vicinity of the frame 24. In such a case, the frame 24 need only be moved laterally along the workpiece 10 to the next predetermined location of the workpiece that is to be inspected. In such a case, it is possible that the workpiece 10 can be inspected in significantly shorter time periods than with conventional non-destructive inspection techniques.

In other embodiments, the frame 24 has mounted thereon fewer than the number of the non-destructive inspection sensors 38 entailed to inspect substantially all of the workpiece 10 in the vicinity of the frame 24. In such embodiments, after a section of a predetermined location of the workpiece has been inspected, the frame 24 can be translated in a desired manner, such as axially, longitudinally, or the like, to move the non-destructive inspection sensors 38 to another section of the predetermined location of the workpiece 10 that is being inspected. To that end, a translation device 40 (not shown in FIG. 2) is mounted on the transport device 20. After all desired sections of the predetermined location of the workpiece 10 have been inspected, then the transport device 20 can be moved to reposition the frame 24 and the non-destructive inspection sensors 38 mounted thereon to a next predetermined location of the workpiece 10 that is to be inspected. Any type of translation device may be used as desired to translate the frame 24 about the predetermined location of the workpiece 10. Given by way of non-limiting example, the translation device 40 may be a linear motor or the like.

As discussed above, any type of non-destructive inspection sensor whatsoever can be used as desired for a particular application. To that end, the type of non-destructive inspection sensor 38 used may depend in part on the material used for the workpiece 10 and may further depend in part on the type of characteristic to be inspected. Also as discussed above, more than one type of non-destructive inspection sensor can be mounted on the frame 24. In addition, the non-destructive inspection sensors can be one-sided non-destruction inspection sensors, and/or non-destruction inspection sensors that are associated with area inspection methods, and/or non-destruction inspection sensors that entail access to both sides of a workpiece.

With this context in mind, the following exemplary-types of non-destructive inspection sensors may be used in embodiments as desired. The following types of non-destructive inspection sensors are given by way of non-limiting example and are not intended to be limited whatsoever.

A. One-Sided Non-Destructive Inspection Sensors

One-sided non-destructive inspection sensors may be used for inspecting the workpiece 10. The one-sided non-destructive inspection sensors may entail continuous movement and tracking, or sequential movement and tracking, or sequential movement with data collection that can be tracked positionally.

For example, exemplary ultrasonic transducers can be used for pulse echo ultrasound, pitch-catch ultrasound, guided-wave ultrasound, acousto-ultrasound, backscatter ultrasound, and the like, for providing inspection for disbonds, delaminations, wrinkles, heat damage, and porosity measurement in composites and thinning in metals. The ultrasonic transducers can be contact or non-contact (such as air coupled) transducers, and may include laser ultrasound. The ultrasonic transducers can be single transducers, transducer pairs, or arrays of various configurations. The ultrasonic transducers entail continuous movement and tracking.

As another example, exemplary one-sided non-destructive inspection sensors may include those used for digital acoustic video inspection and acoustography inspection. These sensors may be used for composite inspection. These one-sided non-destructive inspection sensors may entail continuous movement and tracking or sequential movement and tracking.

As another example of one-sided non-destructive inspection sensors, low frequency ultrasonic sensors, such as a mechanical impedance analysis (MIA) probe, ultrasonic resonance probe, or sondicator probe, can be used for disbond or delamination detection in sandwich structures and laminates. These one-sided non-destructive inspection sensors entail continuous movement and tracking.

As another example of one-sided non-destructive inspection sensors, resonance acoustic method (RAM) "tappers" can be used to perform mechanical tap testing for disbond or delamination detection in laminate composites. Two RAM sensors are shown as the non-destructive inspection sensors 38 in FIG. 3. As shown in FIG. 3, each RAM sensor includes a spherical striker 42 to strike or tap the exterior surface of the workpiece 10 and a microphone 44. In one embodiment, the RAM sensors can be translated in one inch increments by the translation device 40 until the section of the predetermined location of the workpiece 10 is inspected. Then, the RAM sensors can be moved laterally by the transport devices 20 in one a inch increment and the inspection and translation process repeated until inspection of the workpiece 10 is complete. Thus, the RAM sensors entail continuous movement and tracking.

As another example of one-sided non-destructive inspection sensors, remote acoustic impact Doppler (RAID) sensors can be used for inspection of composite and metal bonds and corrosion detection. These one-sided non-destructive inspection sensors entail continuous movement and tracking.

As another example of one-sided non-destructive inspection sensors, microwave sensors can be used for composite defect inspection in thick, ultrasonically-attenuative materials such as structural foams. These one-sided non-destructive inspection sensors may entail continuous movement and tracking or sequential movement and tracking.

As another example of one-sided non-destructive inspection sensors, eddy current or similar electro-magnetic sensors can be used for finding cracks and thinning in metals, verifying lightning strike protection, assessing heat damage, and the like. These one-sided non-destructive inspection sensors entail continuous movement and tracking.

As another example of one-sided non-destructive inspection sensors, optical sensors or lasers can be used for inspection of weld profiles in metals and geometric configurations in general. These one-sided non-destructive inspection sensors entail continuous movement and tracking.

As another example of one-sided non-destructive inspection sensors, x-ray backscatter sensors can be used for crack detection, corrosion detection, and internal configuration verification. These one-sided non-destructive inspection sensors entail sequential movement with data collection that can be tracked positionally.

As another example of one-sided non-destructive inspection sensors, photon induced positron annihilation (PIPA) sensors can be used to inspect for metal and composite pre-crack damage and local stress states. These one-sided non-destructive inspection sensors entail sequential movement with data collection that can be tracked positionally.

B. Area Inspection

Embodiments can also employ area inspection modalities that entail sequential movement and data collection that can be tracked positionally. As a first example of area inspection, laser shearography sensors can be used to rapidly inspect thin-skin composites for disbonds. As another example of area inspection, infrared thermography sensors (including sensors for induction infrared, vibro-thermography, and the like) can be used to inspect for disbonds, voids, and foreign object detection in composite structure.

C. Two-Sided Access

Embodiments can also employ non-destructive inspection techniques that entail access to internal as well as external surfaces of the workpiece 10. In cases where a source is mounted to the frame 24, the sensor may be held in place via magnetically coupling to the frame 24.

As a first example of non-destructive inspection techniques that entail access to internal as well as external surfaces of the workpiece 10, ultrasonic contact and non-contact sensors can be used for through-transmission ultrasonics (TTU). This technique entails continuous movement and tracking.

Digital x-ray inspection is another example of a non-destructive inspection technique that entails access to internal as well as external surfaces of the workpiece 10. In this case, an x-ray source is mounted to the frame 24 (that is, exterior to the workpiece 10. Digital x-ray sensors are located inside the workpiece 10 and are held in place via magnetically coupling to the frame 24. Digital x-ray inspection may be used for crack or foreign object detection. This two-sided inspection technique may entail continuous movement and tracking or sequential movement and tracking.

Neutron radiography is another example of a non-destructive inspection technique that entails access to internal as well as external surfaces of the workpiece 10. In this case, a shielded neutron point source is mounted to the frame 24 (that is, exterior to the workpiece 10. Neutron detectors are located inside the workpiece 10 and are held in place via magnetically coupling to the frame 24. Neutron radiography inspection may be used for crack, void, or foreign object detection. This two-sided inspection technique may entail continuous movement and tracking or sequential movement and tracking.

Through-transmission infrared thermography is another example of a non-destructive inspection technique that entails access to internal as well as external surfaces of the workpiece 10. In this case, an infrared source is mounted to the frame 24 (that is, exterior to the workpiece 10. Infrared sensors are located inside the workpiece 10 and are held in place via magnetically coupling to the frame 24. Through-transmission infrared thermography inspection may be used for disbond, void, or foreign object detection. This two-sided inspection technique may entail sequential movement and data collection that can be tracked positionally.

It will be appreciated that the non-destructive inspection sensors 38 discussed herein can also be applied to features on the workpiece 10 under inspection, such as fastener holes, fasteners, lightning strike protection, appliqué, coatings, bonded sub-structure, and the like. The position of the sensors 38 employed in this manner could be tracked in the same manner as discussed above.

Figure 4:
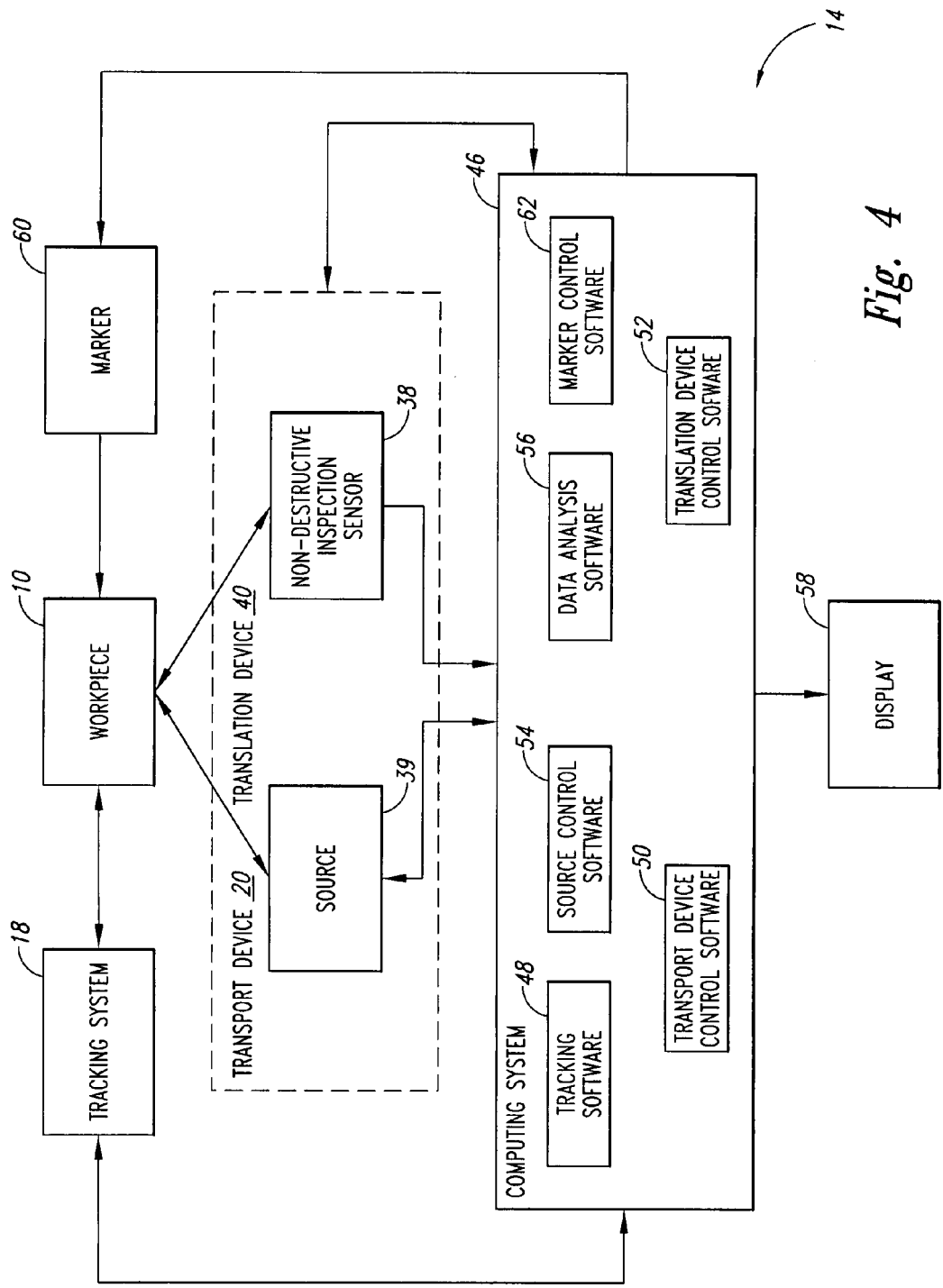
FIG. 4 is a block diagram of an exemplary system.

Referring now to FIG. 4, the tracking system 18 is operatively coupled in data communication with a computing system 46. The computing system 46 includes tracking software 48 that determines position of the workpiece 10, the transport device 20, the frame 24, and/or the non-destructive inspection sensors 38 being tracked via the fiducials 16, 22, and/or 36. Given by way of non-limiting example, suitable tracking software includes "Spatial Analyzer" software from New River Kinematics.

The computing system 46 also includes transport device control software 50 that controls movement of the transport device 20. The transport device control software 50 cooperates with the tracking software 48. Movement of the transport device 20 to a predetermined location of the workpiece 10 is controlled responsive to data regarding the position of the transport device 20 or the frame 24 or the non-destructive inspection sensors 38 that is provided by the tracking system 18 and the tracking software 48. In one exemplary embodiment, functionality of the transport device control software 50 can also be provided by "Spatial Analyzer" software from New River Kinematics.

The computing system 46 can also include translation device control software 52. The translation device control software 52 can be provided when the translation device 40 is provided to translate the frame 24 about the workpiece 10, thereby translating position of the non-destructive inspection sensors 38. The translation device control software 52 suitably can be a relatively simple, low-level script. For example, in an exemplary embodiment, when "Spatial Analyzer" software from New River Kinematics is used for the tracking software 48 and/or the transport device control software 50, the translation device control software 52 may be a "Spatial Analyzer" script.

The computing system 46 includes source control software 54. The source control software 54 can control energizing and de-energizing of the sources 39. If desired, the source control software 54 can also control sequencing of the sources 39, such as without limitation controlling a tapping sequence when the sources 39 include resonant acoustic method strikers. The source control software 54 suitably can be a relatively simple, low-level script. For example, in an exemplary embodiment, when "Spatial Analyzer" software from New River Kinematics is used for the tracking software 48 and/or the transport device control software 50, the source control software 54 may be a "Spatial Analyzer" script.

The computing system 46 includes data analysis software 56. The data analysis software 56 analyzes sensor data provided by the non-destructive inspection sensors 38 regarding characteristics of the workpiece 10. For example, the data analysis software 56 can cause measurement data from the non-destructive inspection sensors 38 to be displayed on a display device 58. In one exemplary embodiment, the data analysis software 56 can be "Spatial Analyzer" software from New River Kinematics. In such a case, the data analysis software 56 can generate a three-dimensional "porcupine"-type chart for display on the display device 58. In addition, if desired a thermal color graph may be included with an inspection report. Because upper and lower tolerances are well defined, in such a graph any part within tolerance is shown in a "green" zone, and any part outside tolerance is shown in a "red" zone and may be listed and documented as rejectable. The data analysis software 56 can retrieve predetermined threshold criteria for a characteristic for a workpiece of a particular material and compare the measured characteristic against the predetermined threshold characteristic. If the measured characteristic falls within a certain range of values, then the data (and the associated location of the workpiece 10) can be flagged for further investigation and/or action as desired. If the measured characteristic falls outside the predetermined threshold, then the data (and the associated location of the workpiece 10) can be flagged for further inspection and/or repair as desired. Because position of the sensors 38 has been precisely tracked (in relationship to the part reference system), the exact location of the flawed areas is recorded and can be precisely located again and repaired, if desired. Thus, any desired repairs can be effected—even if the part itself is not marked.

In the event that a measured characteristic falls within a certain range of values or outside the predetermined threshold, then in some embodiments the associated location on the workpiece 10 can be marked with a marker 60. For example, exemplary through-transmission ultrasound sensors include a built-in part marker. Further, the computing 60 can include marker control software 62. The data analysis software 56 can provide data regarding a measurement that falls within a certain range of values or outside the predetermined threshold criteria (and its associated location on the workpiece 10) to the marker control software 62. The marker control 62 can then cause the marker 60 to mark the workpiece in the associated location in an appropriate manner. For example, a location may be marked to indicate caution or further follow-up action, such as by being marked in yellow. As another example, a location may be marked to indicate a repair action is entailed, such as by being marked in red.

Figure 5:
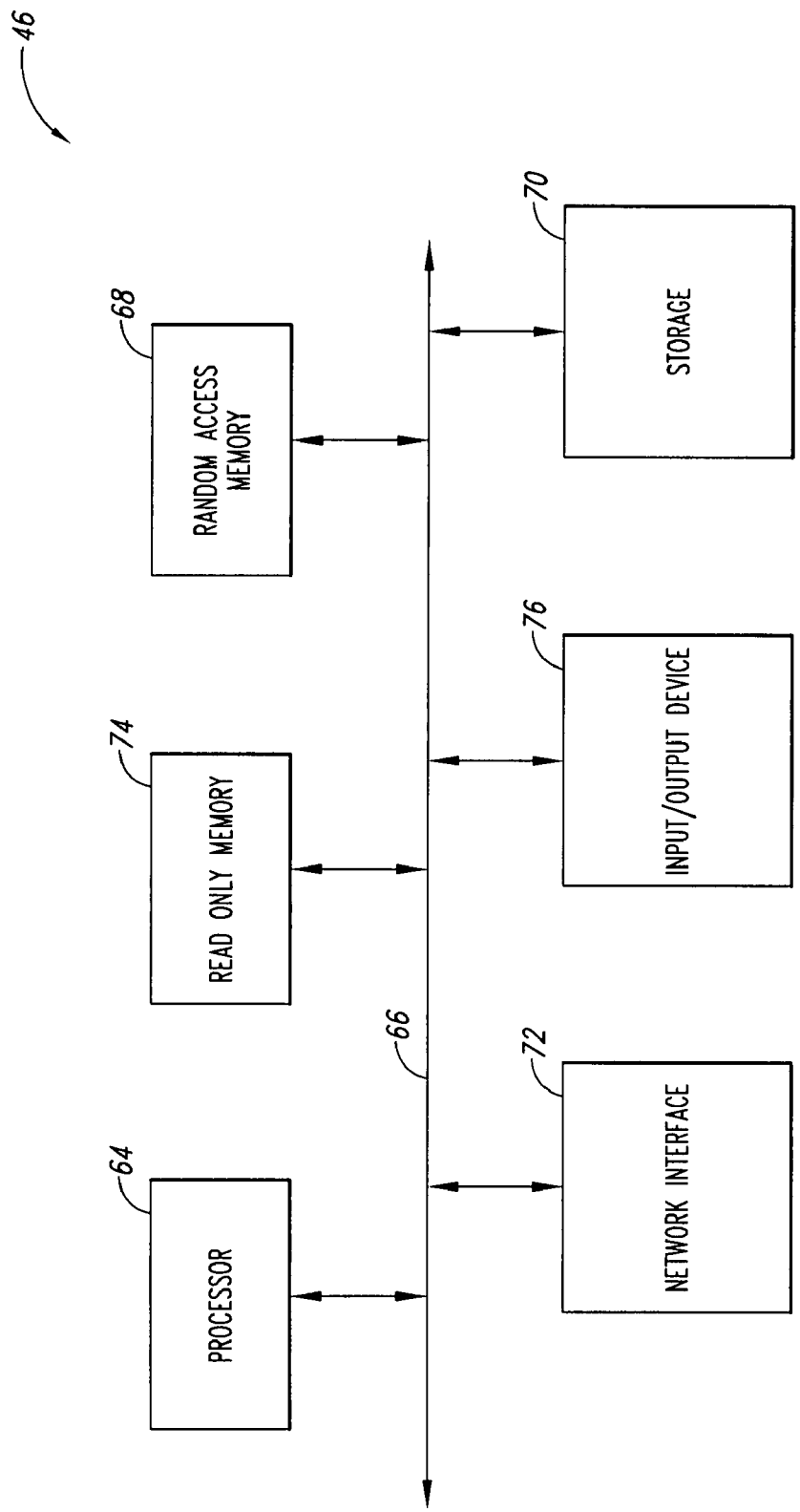
FIG. 5 is a block diagram of an exemplary computing system.

Referring now to FIG. 5, a typical computing system 46 (that also may be referred to as a host computer or system) utilized in an embodiment includes a central processing unit ("CPU") (or microprocessor) 64 connected to a system bus 66. Random access main memory ("RAM") 68 is coupled to the system bus 66 and provides the CPU 64 with access to memory storage 70 for storing the measured sensor data and analyzed data. When executing program instructions, the CPU 64 stores those process steps in the RAM 68 and executes the stored process steps out of the RAM 68.

The computing system 46 connects to a computer network (not shown) via a network interface 72 and through a network connection (not shown). One such network is the Internet that allows the computing system 46 to download applications, code, documents and other electronic information.

Read only memory ("ROM") 74 is provided to store invariant instruction sequences such as start-up instruction sequences or basic input/output operating system (BIOS) sequences.

An Input/Output ("I/O") device interface 76 allows the computing system 46 to connect to various input/output devices, for example, a keyboard, a pointing device ("mouse"), a monitor, printer, a modem, and the like. The I/O device interface 76 is shown as a single block for simplicity and may include several interfaces to interface with different types of I/O devices.

It will be appreciated that embodiments are not limited to the architecture of the computing system 46 shown in FIG. 5. Based on the type of applications/business environment, the computing system 46 may have more or fewer components. For example, the computing system 46 can be a set-top box, a lap-top computer, a notebook computer, a desktop system, or other types of systems.

Figure 6:
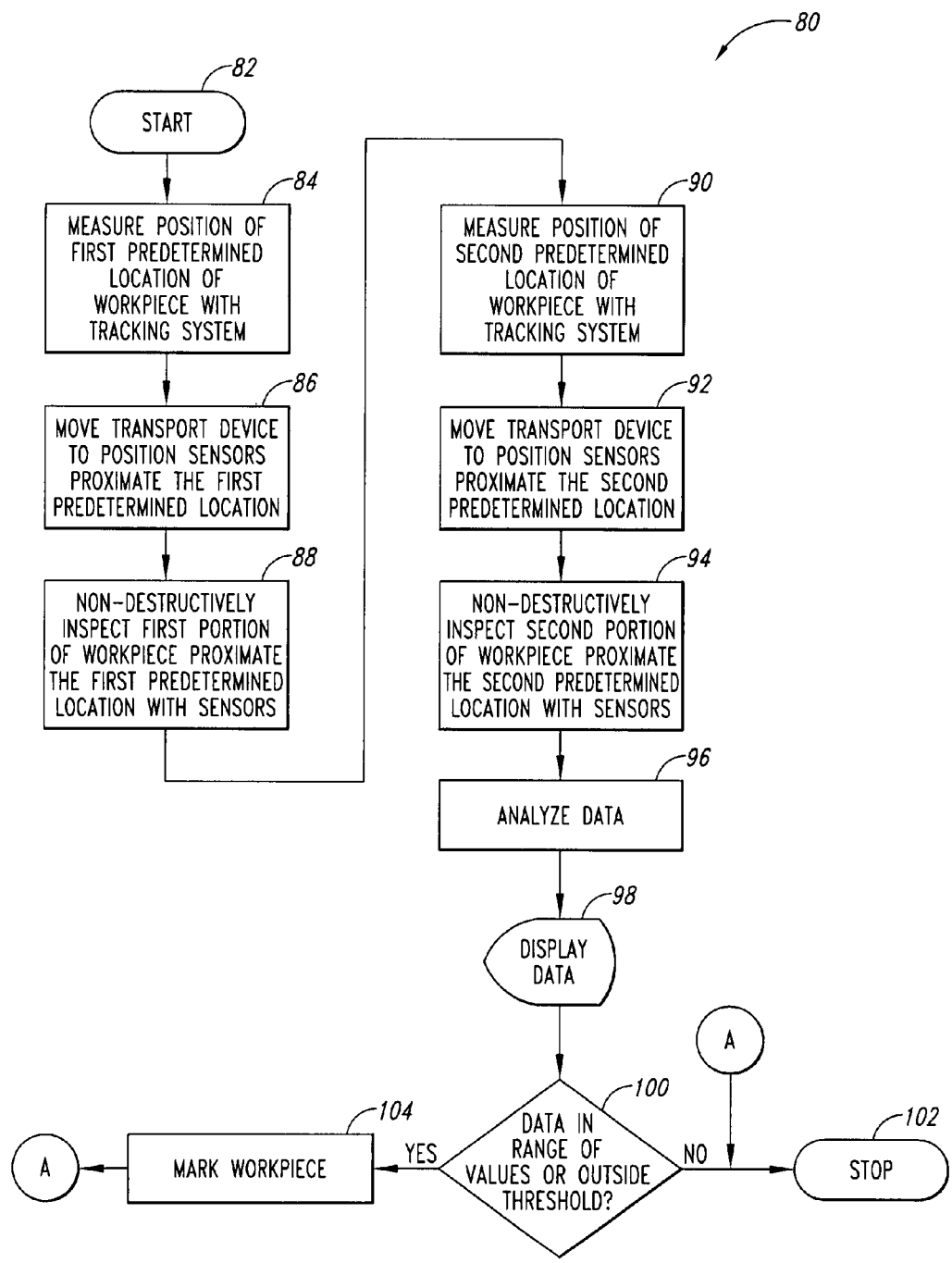
FIG. 6 is a flow chart of an exemplary method for automated inspection of a workpiece.

Referring now to FIG. 6, a method 82 for automated inspection of a workpiece starts at a block 82. The blocks of the method 80 suitably are performed on the workpiece 10 by components of the system 14 as discussed above with reference to FIGS. 2-5. Because the method 80 is completely automated and under the control of the computing system 16, all of the processing blocks discussed below for the method 80 can be carried out without operator intervention. Thus, the method 80 can be performed during a back shift, such as a third shift, midnight shift, or the like, thereby making more efficient use of facility and labor resources.

At a block 84, position of a first predetermined location of a workpiece is measured with a tracking system. At a block 86, the transport device is moved to position the non-destructive inspection sensors proximate the first predetermined location of a workpiece. Position of the transport device, the sensors, and the frame upon which the sensors are mounted are tracked, as desired. At a block 88, a first portion of a workpiece proximate the first predetermined location is non-destructively inspected with the non-destructive inspection sensors.

At a block 90, position of a second predetermined location of a workpiece can be measured with the tracking system. At a block 92, the transport device can be moved to position the non-destructive inspection sensors proximate the second predetermined location of a workpiece. Position of the transport device, the sensors, and the frame upon which the sensors are mounted are tracked, as desired. At a block 94, a second portion of a workpiece proximate the second predetermined location can be non-destructively inspected with the non-destructive inspection sensors.

At a block 96 data from the sensors is analyzed. Data can be provided from the non-destructive inspection sensors to a computing system and the data can be analyzed with the computing system. At a block 98 the data is displayed on a display device.

The data can be compared with predetermined threshold criteria for a workpiece. At a decision block 100, a determination is made whether the data is in a predetermined range of values or is outside a predetermined threshold criteria. If the data is neither in a predetermined range of values nor outside a predetermined threshold criteria, then the method 80 stops at a block 102. If the data is either in a predetermined range of values or outside a predetermined threshold criteria, then at a block 104 a workpiece can be marked in an associated location as appropriate for the measured value, such as a cautionary marking or a marking indicating that a repair action is entailed. As a result, a potential flaw, defect, or the like can be attended to and repaired, thereby helping to prevent flaws, defects, or the like from remaining in material that is incorporated into final assembly of a part or product. The method 80 then stops at the block 102 when all of the workpiece has been inspected as desired.

While a number of exemplary embodiments and aspects have been illustrated and discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A method of automatically inspecting a workpiece, the method comprising:
   providing a plurality of non-destructive inspection sensors mounted on a frame that is on a transport device;
   disposing a plurality of fiducials on a workpiece at a plurality of predetermined locations on the workpiece configured to receive the plurality of fiducials;
   using one or more of the plurality of fiducials, measuring position of a first predetermined location of the workpiece with a tracking system;
   moving the transport device to position the plurality of non-destructive inspection sensors proximate to the first predetermined location of the workpiece;
   non-destructively inspecting a first portion of the workpiece proximate to the first predetermined location with the plurality of non-destructive inspection sensors;
   providing data from the plurality of non-destructive sensors to a computing system;
   analyzing the data with the computing system by comparing the data to predetermined threshold criteria for the workpiece; and
   when analyzed data for an associated location is outside the predetermined threshold criteria for the workpiece, directing a marking device under control of the computing system to mark the workpiece at the associated location.

2. The method of claim 1, wherein moving the transport device includes measuring position of the frame with the tracking system.

3. The method of claim 1, wherein moving the transport device includes measuring position of the transport device with the tracking system.

4. The method of claim 1, further comprising:
   measuring position of a second predetermined location of the workpiece with the tracking system;
   moving the transport device to position the plurality of non-destructive inspection sensors proximate the second predetermined location of the workpiece; and
   non-destructively inspecting a second portion of the workpiece proximate to the second predetermined location with the plurality of non-destructive inspection sensors.

5. The method of claim 1, further comprising disposing a second plurality of fiducials on the frame and the transport device.

6. The method of claim 1,
   further comprising including a hole in the exterior of the workpiece to receive one or more of the plurality of fiducials at one or more of the locations.

7. A method of automatically inspecting a workpiece, the method comprising:
   providing a plurality of non-destructive inspection sensors mounted on a frame that is mounted on a transport device;
   disposing a plurality of fiducials on a workpiece at a plurality of predetermined locations;
   measuring position of a first predetermined location of the workpiece with a tracking system using one of more of the plurality of fiducials;
   moving the transport device to position the plurality of non-destructive inspection sensors proximate the first predetermined location of the workpiece;
   non-destructively inspecting a first portion of the workpiece proximate the first predetermined location with the plurality of non-destructive inspection sensors;
   measuring position of a second predetermined location of the workpiece with the tracking system;
   moving the transport device to position the plurality of non-destructive inspection sensors proximate the second predetermined location of the workpiece;
   non-destructively inspecting a second portion of a workpiece proximate the second predetermined location with the plurality of non-destructive inspection sensors;
   providing data from the plurality of non-destructive sensors to a computing system; and
   analyzing the data with the computing system.

8. The method of claim 7, wherein moving the transport device includes measuring position of the frame with the tracking system.

9. The method of claim 7, wherein moving the transport device includes measuring position of the transport device with the tracking system.

10. The method of claim 7, further comprising disposing a plurality of fiducials on the frame and the transport device.

11. The method of claim 7, wherein analyzing the data includes comparing the data with predetermined threshold criteria for the workpiece.

12. The method of claim 11, further comprising marking the workpiece in an associated location when analyzed data for the associated location is outside the predetermined threshold criteria.

13. The method of claim 7, wherein one or more of the plurality of predetermined locations on the workpiece are configured to receive one or more of the plurality of fiducials on an exterior of the workpiece.

14. The method of claim 13, wherein the one or more of the plurality of predetermined locations on the workpiece include a hole in the exterior of the workpiece to receive one or more of the plurality of fiducials at one or more of the predetermined locations.

15. A system for automatically inspecting a workpiece, the system comprising:
a plurality of fiducials disposed on a workpiece at a plurality of predetermined locations;
a tracking system that measures a position of an associated location on the workpiece using one or more of the plurality of fiducials;
a transport device;
a frame that is mounted on the transport device, the frame having a shape that accommodates a shape of an exterior of a workpiece to be inspected;
a plurality of non-destructive inspection sensors mounted on the frame; and
a computing system operatively coupled to the tracking system and to the plurality of non-destructive inspection sensors.

16. The system of claim 15, further comprising a plurality of fiducials disposed on the frame and the transport device.

17. The system of claim 15, wherein the computing system includes a first computer processing component configured to control movement of the transport device.

18. The system of claim 17, wherein the computing system includes a second computer processing component configured to analyze data from the plurality of non-destructive inspection sensors.

19. The system of claim 18, wherein the second computer processing component is further configured to compare the data with predetermined threshold criteria for the workpiece.

20. The system of claim 19, further comprising at least one marking device operatively coupled to the computing system, the marking device being configured to mark the workpiece in an associated location when analyzed data for the associated location is outside the predetermined threshold criteria.

21. The system of claim 15, wherein the tracking system includes a laser tracker.

22. The system of claim 15, wherein the tracking system includes a tracking system chosen from a digital photogrammetry system, an optical triangulation system, and an ultrasound system.

23. The system of claim 15, wherein the transport device includes at least one automated guided vehicle.

24. The system of claim 15, wherein the frame has a shape arranged to accommodate an exterior of an aircraft fuselage.

25. The system of claim 15, wherein the frame has a shape arranged to accommodate an exterior of an aircraft wing.

26. The system of claim 15, wherein the plurality of non-destructive inspection sensors includes at least one first sensor for a first type of non-destructive inspection and at least one second sensor for a second type of non-destructive inspection that is different from the first type of non-destructive inspection.

27. The system of claim 15, wherein the plurality of non-destructive inspection sensors includes at least one one-sided non-destructive inspection sensor chosen from an ultrasonic transducer, a digital acoustic video sensor, an acoustography sensor, a mechanical impedance analysis probe, an ultrasonic resonance probe, a sondicator probe, a resonance acoustic mechanical tap tester, a remote acoustic impact Doppler sensor, an eddy current sensor, an optical image sensor, an x-ray backscatter sensor, and a photon induced positron annihilation sensor.

28. The system of claim 17, wherein the plurality of non-destructive inspection sensors includes at least one sensor used to sequentially sense data and chosen from a laser shearography sensor and an infrared thermography sensor.

29. The system of claim 15, wherein the plurality of non-destructive inspection sensors includes at least one sensor disposed on one side of a surface of the workpiece and a source disposed an another side of the surface of the workpiece, the sensor being selected from a through-transmission ultrasonic sensor, a digital x-ray sensor, a neutron radiography sensor, and a through-transmission infrared thermography sensor.

30. The system of claim 15, wherein one or more of the plurality of predetermined locations on the workpiece are configured to receive one or more of the plurality of fiducials on the exterior of the workpiece.

31. The system of claim 30, wherein the one or more of the plurality of predetermined locations on the workpiece include a hole in the exterior of the workpiece to receive one or more of the plurality of fiducials at one or more of the predetermined locations.

32. A system for automatically inspecting a workpiece, the system comprising:
a plurality of fiducials disposed on a workpiece at a plurality of predetermined locations;
a tracking system that measures a position of an associated location on the workpiece using one or more of the plurality of fiducials;
a transport device having a plurality of fiducials disposed thereon;
a frame that is mounted on the transport device, the frame having a shape that accommodates a shape of an exterior of the workpiece to be inspected, the frame having a plurality of fiducials disposed thereon;
a plurality of non-destructive inspection sensors mounted on the frame; and
a computing system operatively coupled to the tracking system and to the plurality of non-destructive inspection sensors, the computing system including:
a first computer processing component configured to control movement of the transport device; and
a second computer processing component configured to analyze data from the plurality of non-destructive inspection sensors.

33. The system of claim 32, wherein the second computer processing component is further configured to compare the data with predetermined threshold criteria for the workpiece.

34. The system of claim 33, further comprising at least one marking device operatively coupled to the computing system, the marking device being configured to mark the workpiece in an associated location when analyzed data for the associated location is outside the predetermined threshold criteria.

35. The system of claim 32, wherein the tracking system includes a laser tracker.

36. The system of claim 32, wherein the tracking system includes a tracking system chosen from a digital photogrammetry system, an optical triangulation system, and an ultrasound system.

37. The system of claim 32, wherein the transport device includes at least one automated guided vehicle.

38. The system of claim 32, wherein the frame has a shape arranged to accommodate an exterior of an aircraft fuselage.

39. The system of claim 32, wherein the frame has a shape arranged to accommodate an exterior of an aircraft wing.

40. The system of claim 32, wherein the plurality of non-destructive inspection sensors includes at least one first sensor for a first type of non-destructive inspection and at least one second sensor for a second type of non-destructive inspection that is different from the first type of non-destructive inspection.

41. The system of claim 32, wherein the plurality of non-destructive inspection sensors include at least one one-sided non-destructive inspection sensor chosen from an ultrasonic transducer, a digital acoustic video sensor, an acoustography sensor, a mechanical impedance analysis probe, an ultrasonic resonance probe, a sondicator probe, a resonance acoustic mechanical tap tester, a remote acoustic impact Doppler sensor, an eddy current sensor, an optical image sensor, an x-ray backscatter sensor, and a photon induced positron annihilation sensor.

42. The system of claim 32, wherein the plurality of non-destructive inspection sensors includes at least one sensor used to sequentially sense data and chosen from a laser shearography sensor and an infrared thermography sensor.

43. The system of claim 32, wherein the plurality of non-destructive inspection sensors includes at least one sensor disposed on one side of a surface of the workpiece and a source disposed an another side of the surface of the workpiece, the sensor being chosen from a through-transmission ultrasonic sensor, a digital x-ray sensor, a neutron radiography sensor, and a through-transmission infrared thermography sensor.

44. The system of claim 32, wherein one or more of the plurality of predetermined locations on the workpiece are configured to receive one or more of the plurality of fiducials on the exterior of the workpiece.

45. The system of claim 44, wherein the one or more of the plurality of predetermined locations on the workpiece include a hole in the exterior of the workpiece to receive one or more of the plurality of fiducials at one or more of the predetermined locations.

* * * * *